United States Patent
Campbell et al.

(10) Patent No.: US 7,410,471 B1
(45) Date of Patent: Aug. 12, 2008

(54) ORTHOSIS KNEE JOINT AND SENSOR

(75) Inventors: James H. Campbell, Clarkston, MI (US); Nicholas Zalinski, Madison Heights, MI (US); Jonathan M. Naft, Chagrin Falls, OH (US); Wyatt S. Newman, Cleveland Heights, OH (US)

(73) Assignee: Becker Orthopedic Appliance Company, Troy, MI (US)

( * ) Notice: Subject to any disclaimer, the term of this patent is extended or adjusted under 35 U.S.C. 154(b) by 824 days.

(21) Appl. No.: 10/396,012

(22) Filed: Mar. 25, 2003

Related U.S. Application Data

(63) Continuation-in-part of application No. 10/205,714, filed on Jul. 26, 2002, now Pat. No. 6,770,045, which is a continuation of application No. 09/398,332, filed on Sep. 17, 1999, now Pat. No. 6,517,503.

(60) Provisional application No. 60/101,084, filed on Sep. 18, 1998.

(51) Int. Cl.
    *A61F 5/00* (2006.01)
(52) U.S. Cl. .............................. 602/16; 602/23; 602/26
(58) Field of Classification Search ................... 602/16, 602/23, 26; 601/5, 34, 35; 607/49; 600/592, 600/595; 623/43–45
See application file for complete search history.

(56) References Cited

U.S. PATENT DOCUMENTS

| | | | |
|---|---|---|---|
| 2,071,711 A | 2/1937 | Sprouls | |
| 2,485,036 A | 10/1949 | Christopher | |
| 2,594,227 A | 4/1952 | Smith | |
| 2,700,772 A | 2/1955 | Davidson | |
| 2,943,622 A | 7/1960 | Nelson | |
| 4,520,804 A | 6/1985 | DiGeorge | |
| 4,745,930 A | 5/1988 | Confer | |
| 4,760,850 A | 8/1988 | Phillips et al. | |
| 4,796,631 A * | 1/1989 | Grigoryev | 607/49 |
| 4,846,842 A | 7/1989 | Connolly et al. | |
| 5,010,774 A | 4/1991 | Kikuo et al. | |
| 5,045,829 A | 9/1991 | Kuramochi et al. | |
| 5,062,857 A | 11/1991 | Berringer et al. | |
| 5,121,742 A | 6/1992 | Engen | |

(Continued)

OTHER PUBLICATIONS

Kenton K. Kaufman, et al., "Energy-Efficient Knee-Ankle-foot Orthosis: A Case Study," Journal of Prosthetics and Orthotics, vol. 8, No. 3 (1996), pp. 79-85.

(Continued)

*Primary Examiner*—Michael A. Brown
(74) *Attorney, Agent, or Firm*—Ryndak & Suri LLP

(57) ABSTRACT

A selectively lockable orthotic joint is provided in which a pressure sensor having a thin layer of variably resistive material generates a control signal when an actuation force is applied to the sensor. An electronic circuit operatively connects the sensor to a mechanical orthotic joint that can be selectively locked and unlocked in response to the control signal. The control signal may be uniform in strength selectively locking and unlocking the joint. The control signal may also be variable in strength wherein the orthotic joint provides increasing or decreasing resistance to motion responsive to a corresponding increase or decrease in control signal strength. The device is suitable for use as a foot/ankle/leg orthotic having a foot sensor which selectively operates a mechanical knee joint.

31 Claims, 9 Drawing Sheets

U.S. PATENT DOCUMENTS

| | | |
|---|---|---|
| 5,121,747 A | 6/1992 | Andrews |
| 5,133,774 A | 7/1992 | Sawamura et al. |
| 5,253,656 A | 10/1993 | Rincoe et al. |
| 5,257,673 A | 11/1993 | Sato et al. |
| 5,267,950 A | 12/1993 | Weddendorf |
| 5,282,460 A | 2/1994 | Boldt |
| 5,311,779 A | 5/1994 | Teruo |
| 5,323,650 A | 6/1994 | Fullen et al. |
| 5,328,446 A | 7/1994 | Bunnell et al. |
| 5,408,873 A | 4/1995 | Schmidt et al. |
| 5,490,831 A | 2/1996 | Myers et al. |
| 5,558,627 A | 9/1996 | Singer et al. |
| 5,608,599 A * | 3/1997 | Goldman .................. 361/283.1 |
| 5,628,722 A | 5/1997 | Solomonow et al. |
| 5,662,693 A | 9/1997 | Johnson et al. |
| 5,670,992 A | 9/1997 | Yasuhara et al. |
| 5,678,448 A | 10/1997 | Fullen et al. |
| 5,779,735 A | 7/1998 | Molino |
| 5,808,540 A | 9/1998 | Wheeler et al. |
| 5,976,063 A | 11/1999 | Joutras et al. |
| 5,977,959 A | 11/1999 | Katsurahira et al. |
| 5,993,400 A | 11/1999 | Rincoe et al. |
| 6,065,789 A | 5/2000 | Nagai et al. |
| 6,174,294 B1 | 1/2001 | Crabb et al. |
| 6,188,229 B1 | 2/2001 | Nakamura |
| 6,191,777 B1 | 2/2001 | Yasuhara et al. |
| 6,316,646 B1 | 11/2001 | Tacke et al. |
| 6,500,138 B1 | 12/2002 | Irby et al. |
| 6,517,503 B1 | 2/2003 | Naft et al. |
| 2002/0022508 A1 | 2/2002 | Ikariko |
| 2002/0022518 A1 | 2/2002 | Okuda et al. |

OTHER PUBLICATIONS

"Foot Force Sensor," Cleveland Medical Devices Inc., Jul. 4, 1998.

* cited by examiner

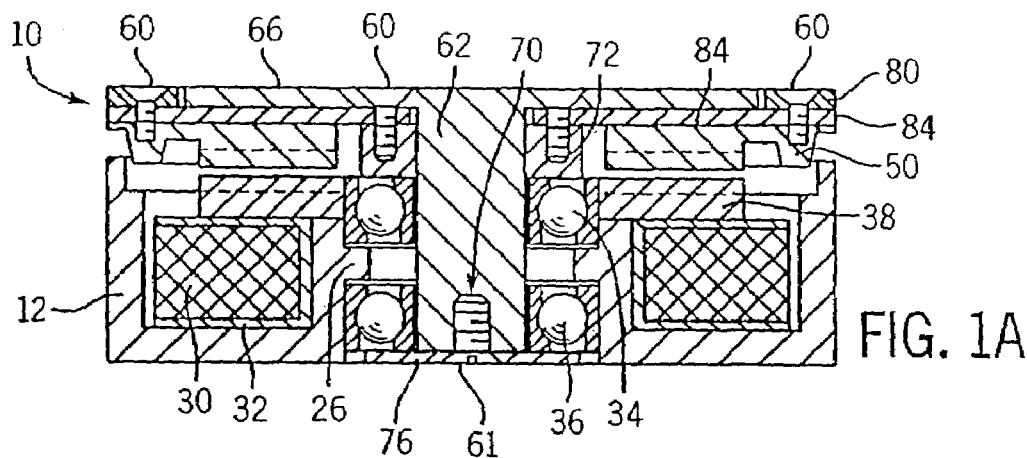
FIG. 1A
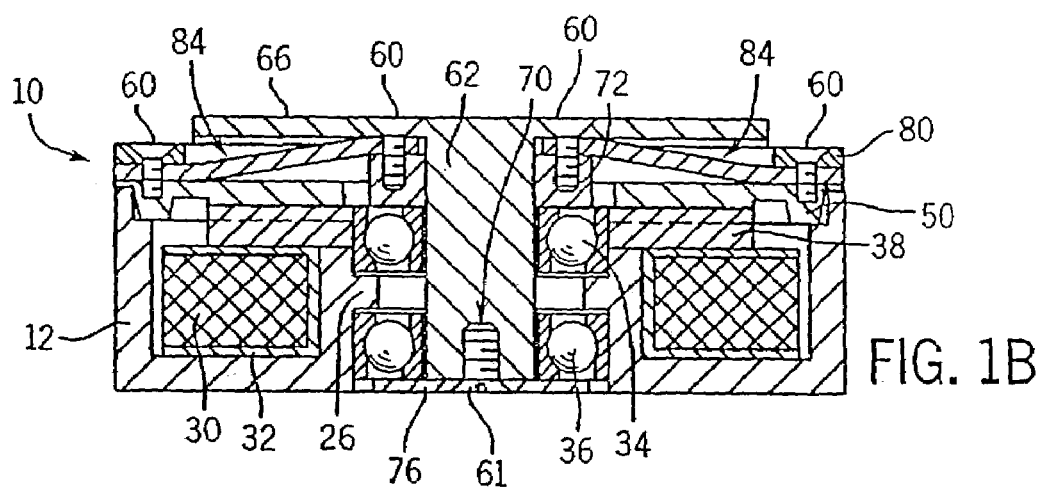
FIG. 1B
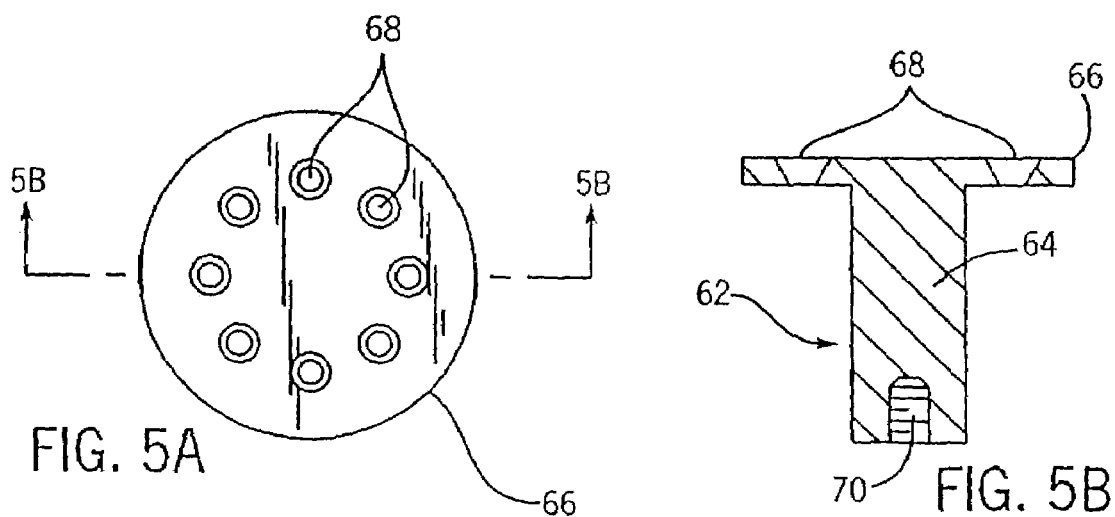
FIG. 5A
FIG. 5B

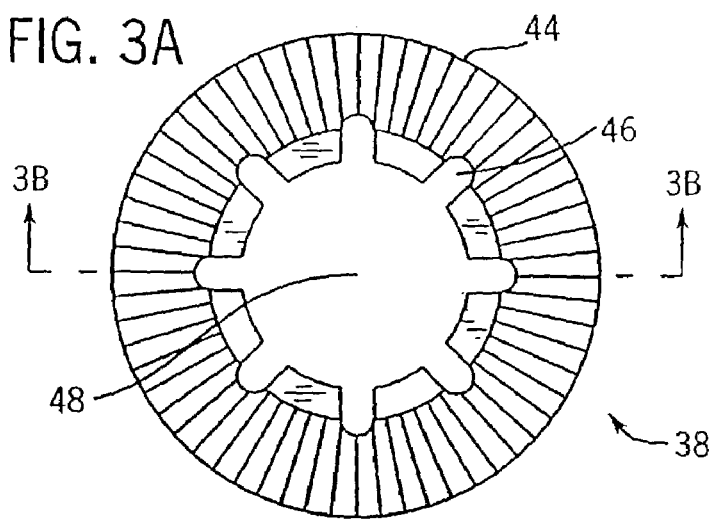
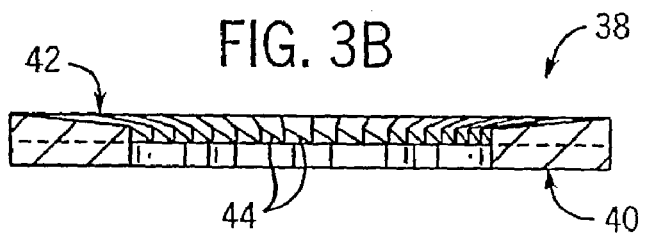
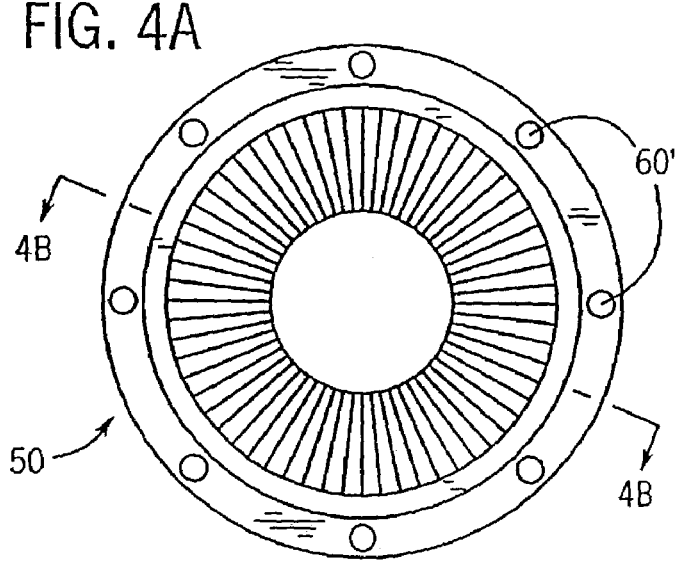
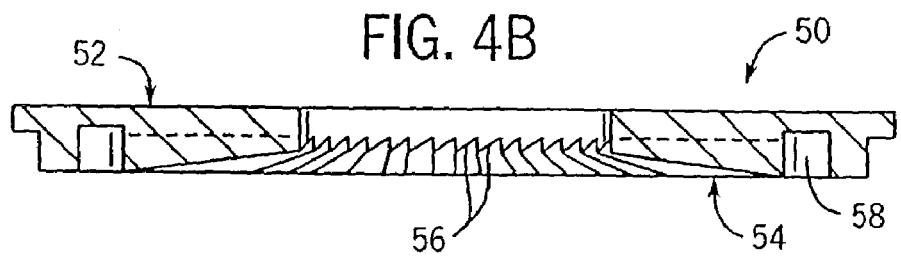

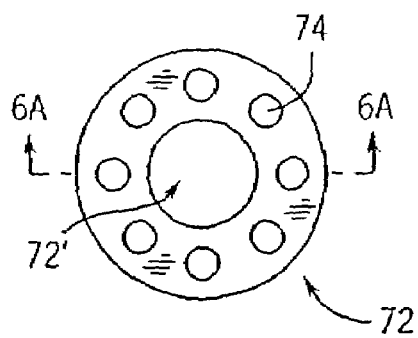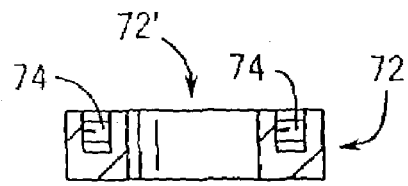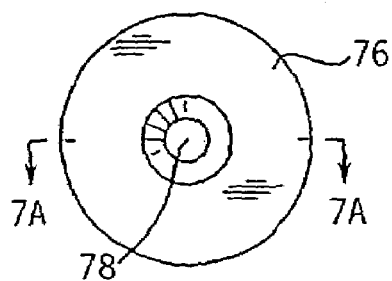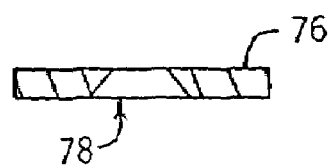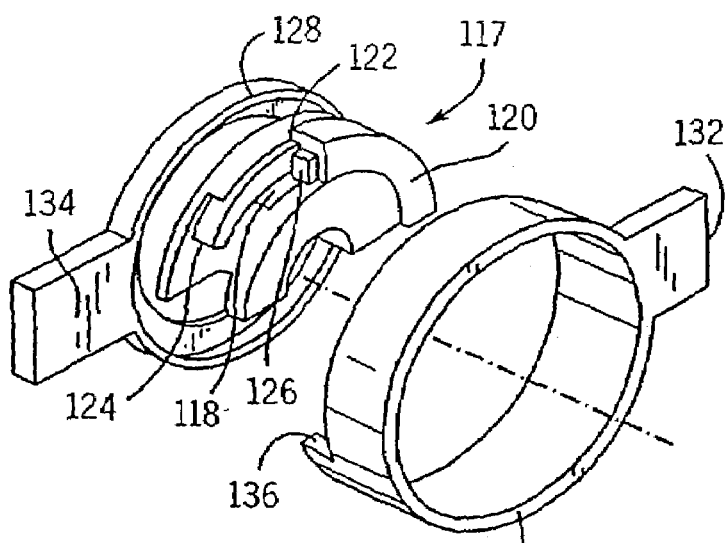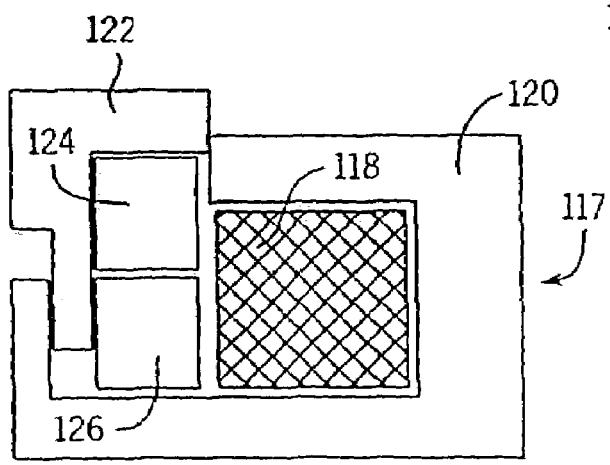

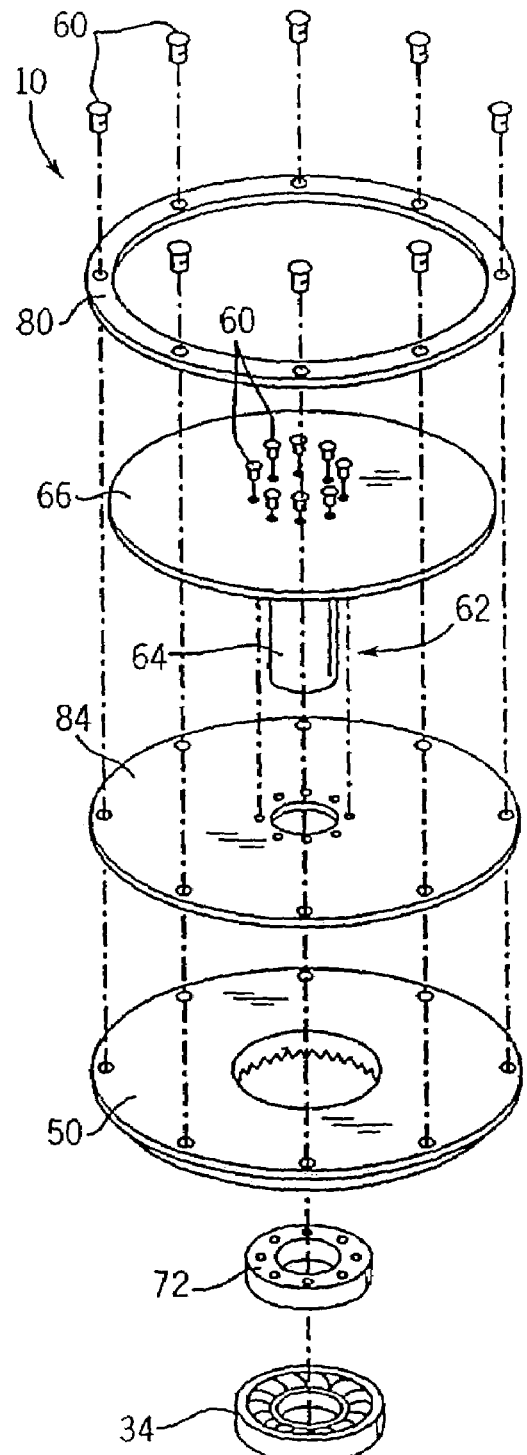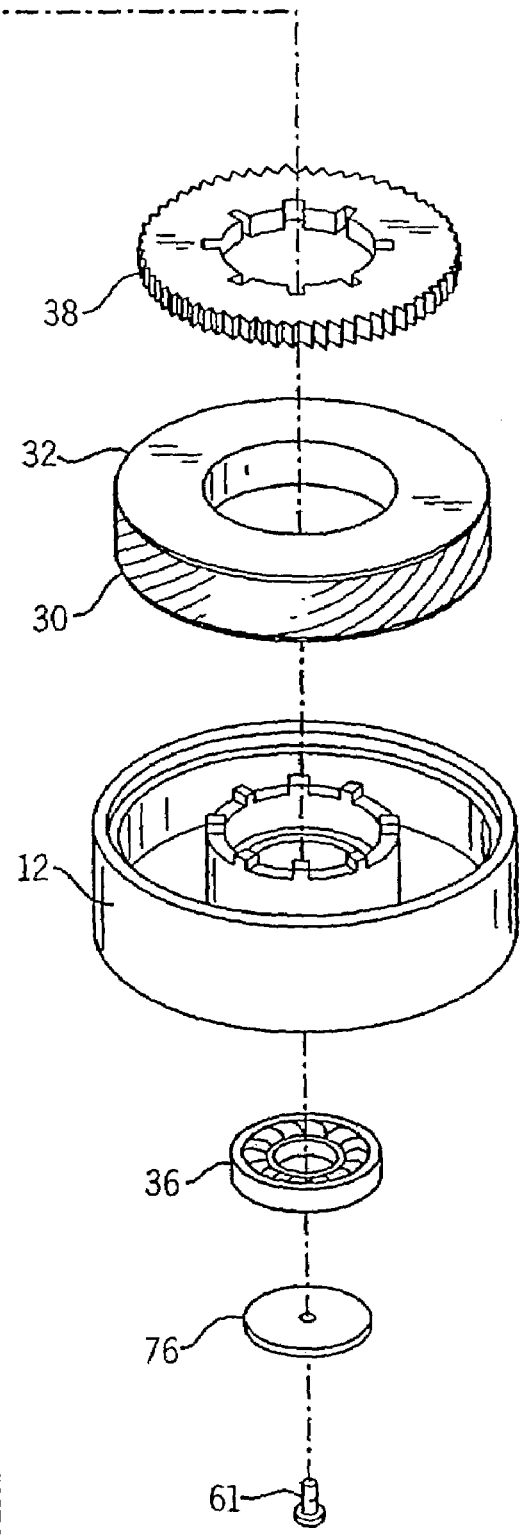
FIG. 10

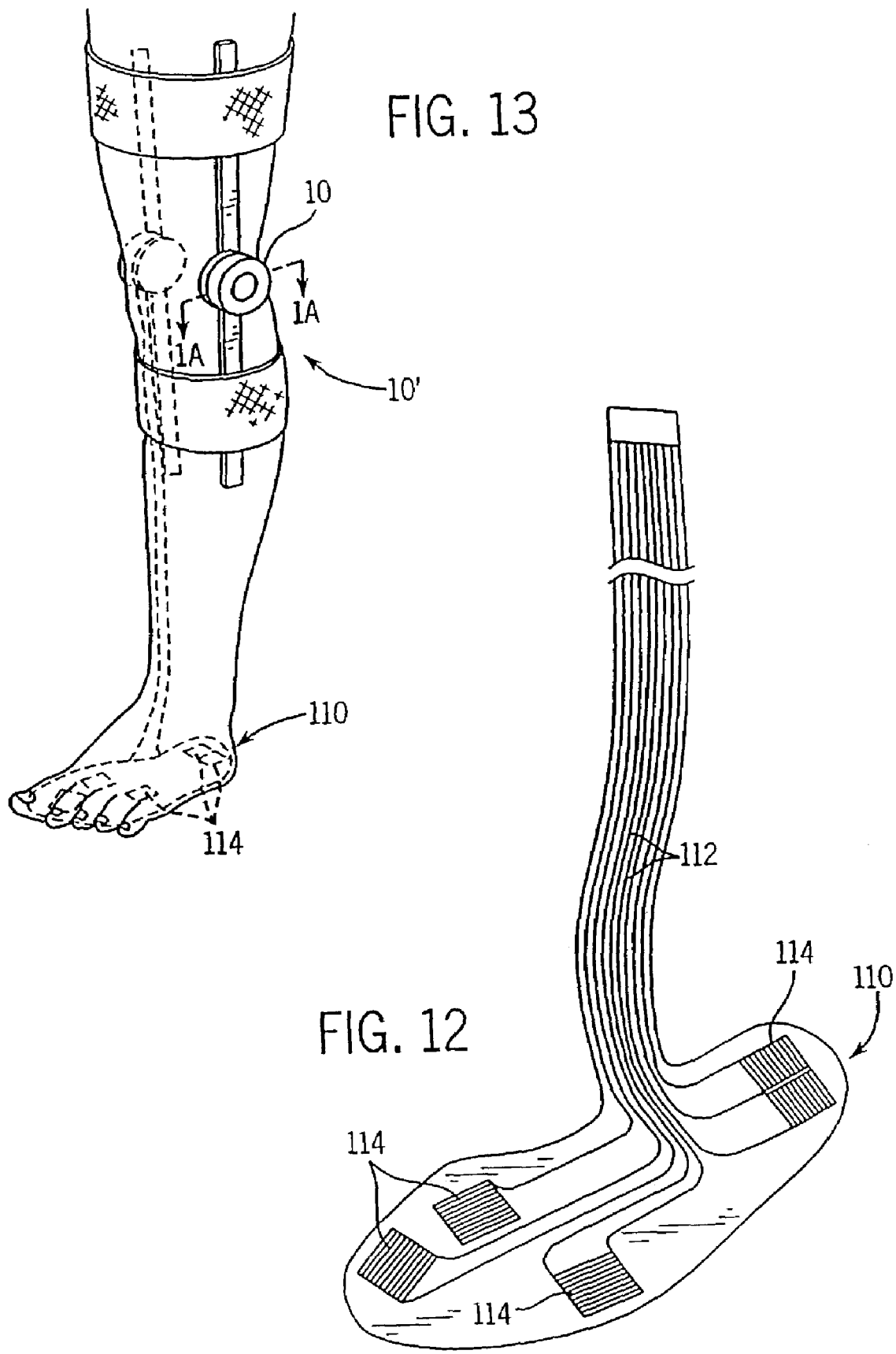

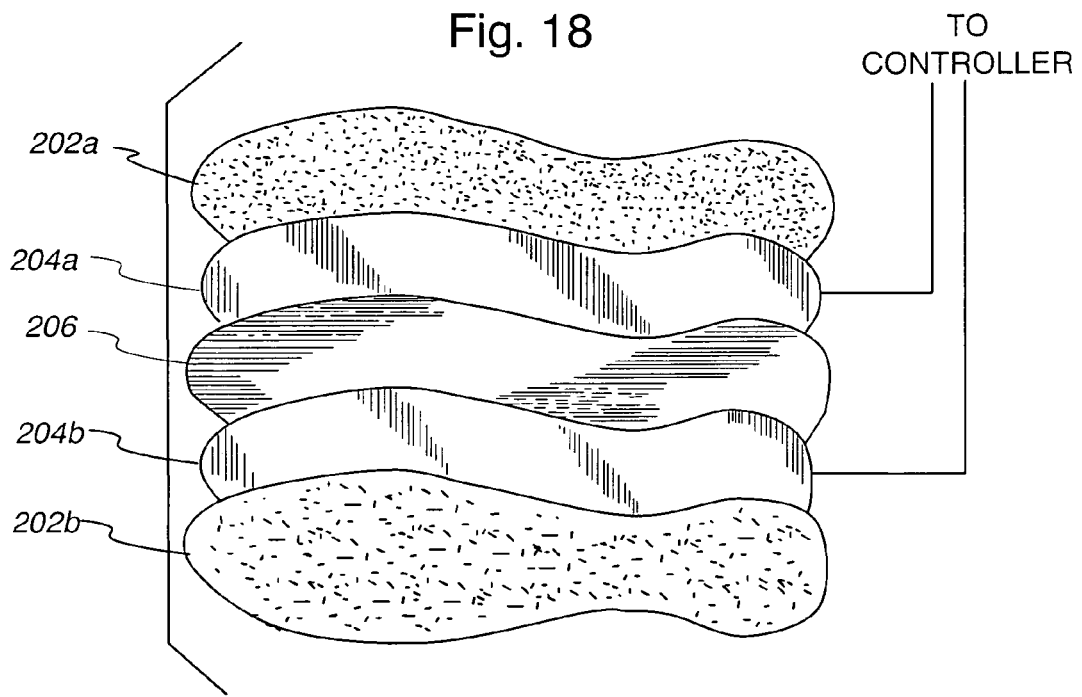
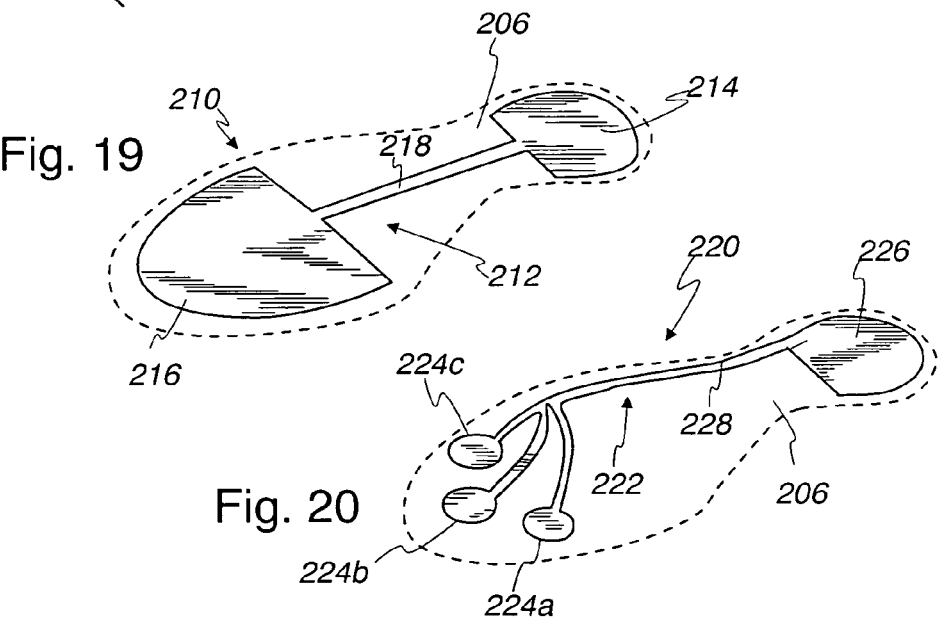

ORTHOSIS KNEE JOINT AND SENSOR

CROSS REFERENCE TO RELATED APPLICATIONS

This is a continuation-in-part of U.S. patent application Ser. No. 10/205,714, filed Jul. 26, 2002, now U.S. Pat. No. 6,770,045 which is a continuation of U.S. patent application Ser. No. 09/398,332, filed Sep. 17, 1999, now U.S. Pat. No. 6,517,503, which claims the benefit under 35 U.S.C. § 119 (e) of U.S. Provisional Application Ser. No. 60/101,084, filed Sep. 18, 1998.

FIELD OF THE INVENTION

This invention relates generally to orthoses for providing assistance in walking. More particularly, the present invention relates to an improved foot sensor and knee joint for such an orthosis.

BACKGROUND OF THE INVENTION

An orthosis is a brace or other orthopedic device that is applied or secured to a segment or part of a human body for the purpose of assisting in the restoration or improvement of its function. Orthoses can provide assistance in walking to persons having any of several types of walking disability. One known type of orthosis is a knee/ankle/foot orthosis which controls the motion and alignment of a knee and an ankle when a person attempts to walk. Such orthoses can be made of molded plastic materials or of metal and leather parts. Various knee and ankle joints can be added to achieve the desired function.

There are many reasons for wearing such an orthosis, including knee injuries, arthritis, stroke, brain injuries, spinal cord injury and post-polio treatment. A person who is not able to properly move his leg and/or knee joint in a sufficiently functional manner to ambulate may wear a knee/ankle/foot orthosis to stabilize his leg and allow for ambulation.

A need exists for an effective knee orthosis that is able to automatically lock and unlock during ambulation without direct manual patient intervention.

BRIEF SUMMARY OF THE INVENTION

In accordance with the present invention, there is provided an orthosis for assistance in walking.

More particularly, in accordance with one aspect of the invention, the orthosis includes an orthosis system which comprises a foot plate including at least one pressure sensor that senses the pressure exerted by a patient's foot on the foot plate, a circuit connected to at least one pressure sensor in the foot plate and a knee joint which is selectively locked and unlocked by the circuit. To this end, the knee joint is electrically operated.

In accordance with the present invention, a selectively lockable orthotic joint is provided that is capable of locking and unlocking during ambulation by the wearer. The selectively lockable orthotic joint includes at least one pressure sensor which can be used to sense a person's weight or a portion thereof, and may be a sensor to be associated with a person's foot, for example. An electronic circuit is provided that is associated with the pressure sensor for generating a control signal indicative of pressure or weight sensed by the sensor. At least one mechanical orthotic joint that incorporates a locking mechanism is included which orthotic joint can be selectively locked and unlocked in response to the control signal.

More particularly, in accordance with one embodiment of the invention, the mechanical orthotic joint of the selectively lockable orthotic joint invention includes an energizable electromagnetic coil, a spring washer deflectable in an axial direction when the electromagnetic coil is energized and an arrangement of first and second plates. The first plate has a face or an operative surface composed of a plurality of spaced teeth. The second plate also has a face or an operative surface having a plurality of spaced teeth that are complementary to the plurality of spaced teeth of the first plate. The second plate is mounted so that it is deflectable in an axial direction such that the plurality of spaced teeth of the second plate can engage the plurality of spaced teeth of the first plate when the electromagnetic coil is energized. The engagement of the first and second plates locks movement of the orthotic joint in at least one direction when the first and second plates are engaged.

In accordance with one embodiment, the first and second plates are complementary and each comprise ratchet plates allowing the orthotic joint to move only in one direction when the joint is in a locked position. More specifically, in one embodiment, when unlocked the orthotic joint is movable in a flexion direction and an extension direction and when the orthotic joint is locked, it is movable only in the extension direction.

The first and second plates may comprise a low hysteresis magnetic material.

In accordance with another aspect of the present invention, a method for selectively locking and unlocking an orthotic joint is provided. One embodiment locks the orthotic joint to permit movement only in the extension direction.

In accordance with another aspect of the invention, any suitable knee joint can be utilized in conjunction with the pressure sensor and electronic circuit as long as the knee joint can be selectively locked and unlocked by operation of the electronic circuit during ambulation by the wearer.

In accordance with the method, an orthotic joint of the type previously described is utilized. Pressure is sensed by the pressure sensor and an electronic control signal is generated with the electronic circuit that is indicative of pressure sensed by the pressure sensor. In response to the electronic control signal, the orthotic joint locks through its locking mechanism.

One advantage of the present invention is the provision of a knee joint which allows patients, who are currently walking stiff legged with a locked knee joint in a knee/ankle/foot orthosis, to walk with a more normal gait.

Another advantage of the present invention is the provision of an orthosis which will make sifting and standing much safer and easier for any patient forced to manually unlock his knee joint.

Still another advantage of the present invention is the provision of an orthosis system that senses the pressure placed by a patient's foot on a foot plate or portion of the orthosis and can automatically trigger a knee joint of the orthosis to lock and unlock. The knee joint will be locked when pressure is placed by the patient's foot on the foot plate, such as pressure above a threshold amount. It will be unlocked when the patient's foot no longer exerts pressure on the foot plate which may be the same or a different pressure from the threshold amount.

In accordance with another aspect of the invention, a selectively lockable orthotic joint is provided. The selectively lockable orthotic joint includes an electronic circuit for providing at least one control signal indicative of a value. At least one mechanical orthotic joint is provided that includes a locking mechanism that is in communication with the circuit. The locking mechanism can be selectively locked and unlocked in response to the control signal. The control signal provided by the electronic circuit can originate from a variety of sources other than by sensing pressure or weight. For example, the control signal can originate from EMG signals in leg muscles, from EEG signals, from a sensor that detects distance between the ground and the bottom of a shoe or other article, such as a cane, for example. In addition, a controller could be provided for operation by the user, such as a joy stick or other type of switch in order to generate or otherwise provide the control signal for locking and/or unlocking the locking mechanism of the mechanical orthotic joint.

In accordance with another aspect of the invention, the control signal is generated responsive to a compressive force detected by a pressure sensitive foot sensor. The foot sensor includes a layer of variably resistive material which resistance changes, typically decreases, in electrical resistance when a compressive force having a force component above a threshold force normal to the layer is applied thereto. The variably resistive material becomes conductive upon the application of a force above a threshold force whereupon conductive elements in communication with either side of the variably resistive material close the circuit thereby generating the control signal. The variably resistive material may have either uniform or variable resistance resulting in either a uniform or variable control signal. In one embodiment of the invention, presence of the uniform control signal locks the mechanical joint and absence of the uniform control signal unlocks the joint.

In an alternative embodiment, an orthosis composed of a foot sensor and an electronic circuit that generates a signal or signals proportional to or related to the force sensed by the foot sensor, together with any suitable knee joint as may be known in the art capable of providing varying degrees of resistance to movement or rotation is provided in which a variable control signal proportional to the force applied to the foot sensor may either resistively close the mechanical joint (increase the resistance to movement of the joint) or fully lock the mechanical joint. As greater force is applied to the sensor, the control signal increases in strength increasing the resistance to movement of the mechanical joint or locking the joint altogether. A decrease in the force applied to the sensor reduces the resistance of the mechanical joint with an absence of the control signal or a signal below a threshold eliminating all resistance.

In accordance with another aspect of the invention, the conductive elements are shaped to contact the variably resistive material at discrete zones. The zones correspond to contact points along the underside of the foot and may include a heel zone, a metatarsal zone and a toe zone. Each region may be further divided into sub-zones.

In accordance with another aspect of the invention, the variably resistive material may be divided into discrete regions as desired, for example, corresponding to contact areas of the foot such as the toe region, the metatarsal region and the heel region. The regions may have differing threshold forces. Each region may also be configured to generate either a uniform or variable control signal based on the needs of the orthotic wearer.

Still other benefits and advantages of the invention will become apparent to those of average skill in the art upon a reading and understanding of the following detailed specification.

BRIEF DESCRIPTION OF THE DRAWINGS

The invention may take physical form in certain parts and arrangements of parts, various preferred embodiments of which will be described in detail in this specification and illustrated in the accompanying drawings which form a part hereof and wherein:

FIG. 1A is a side elevational view in cross section along line 1A-1A of FIG. 13 of a knee joint according to the present invention in an unlocked condition;

FIG. 1B is a side elevational view in cross section of the knee joint of FIG. 1A in a locked condition;

FIG. 3A is a top plan view of a bottom ratchet plate of the knee joint of FIG. 1A;

FIG. 3B is a side elevational view in cross section along line 3B-3B of FIG. 3A;

FIG. 4A is a bottom plan view of a top ratchet plate of the knee joint of FIG. 1A;

FIG. 4B is a side elevational view in cross section along line 4B-4B of FIG. 4A;

FIG. 5A is a top plan view of the top end portion of the knee joint of FIG. 1A;

FIG. 5B is a side elevational view in cross section taken along line 5B-5B of FIG. 5A;

FIG. 6 is a top plan view of an inner retaining ring of the knee joint of FIG. 1A;

FIG. 6A is a cross-sectional view along lines 6A-6A of FIG. 6;

FIG. 7 is a top plan view of the retaining cap of the knee joint of FIG. 1A;

FIG. 7A is a cross-sectional view along line 7A-7A of FIG. 7;

FIG. 10 is an exploded perspective view of components of the knee joint of FIG. 1A;

FIG. 12 is a perspective view of the force or pressure sensor employed with the joint of FIG. 1A;

FIG. 13 is a perspective view of an orthosis in accordance with the invention incorporating the joint of FIG. 1A and the sensor of FIG. 12;

FIG. 14 is a fragmentary perspective exploded view of an alternate embodiment joint in accordance with the invention;

FIG. 15 illustrates a cross-sectional schematic view of a portion of the alternate embodiment of FIG. 14;

FIG. 18 is an exploded schematic view of the foot sensor of FIG. 16;

FIG. 19 is a perspective view of an alternate embodiment of the foot sensor in accordance with the present invention; and FIG. 20 is a perspective view of an alternate embodiment of the foot sensor in accordance with the present invention.

DETAILED DESCRIPTION OF THE PREFERRED EMBODIMENT

Figure 2A:
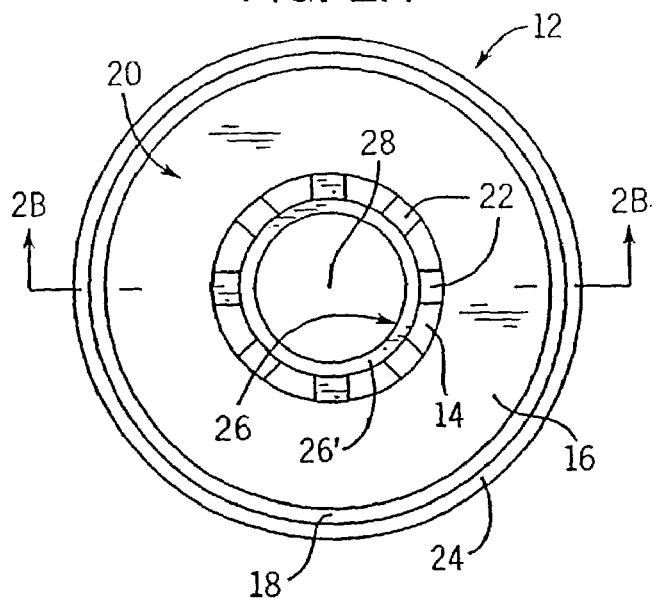
FIG. 2A is a top plan view of the toroidally shaped housing of the joint of FIG. 1A.

Referring now to the drawings wherein the drawings are for purposes of illustrating preferred embodiments of the invention only and not for purposes of limiting same, FIGS. 1A and 1B, 10 and 13, for example, show a knee joint 10 which is used in an orthosis 10' or orthopedic appliance, for example in FIG. 13. It is evident that two such knee joints would need to be employed for the two legs of a patient, one joint for each leg of the patient. Perhaps, even four knee joints could be used, one on either side of the knee of each leg of the patient. It is to be understood that joint 10 could be used other than as a knee joint, for example.

Figure 2B:
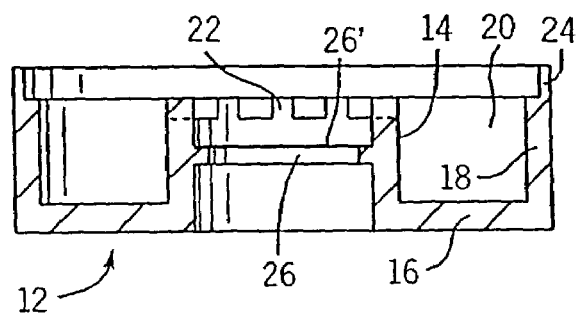
FIG. 2B is a cross-sectional view taken along line 2B-2B of FIG. 2A.

Joint 10 includes a toroidally shaped housing 12. Toroidally shaped housing 12 is depicted individually in FIGS. 2A and 2B. With reference now to FIGS. 2A and 2B, the toroidally shaped housing 12 has an inner wall 14, a base wall 16 and an outer wall 18 which together define a cavity 20. A plurality of spaced teeth 22 protrude upwardly from the inner wall 14. Preferably, eight such teeth are provided, although any suitable number of teeth can be utilized. A continuous flange 24 extends upwardly from the outer wall 18. A rib 26 extends radially inwardly from the inner wall 14 into a central opening 28 to form a toroidal ledge 26' approximately half way up the height of the inner wall.

With reference again to FIGS. 1A and 1B and 10, an electromagnetic coil 30 is located in cavity 20. Electromagnetic coil 30 is formed around a plastic bobbin 32. Positioned on either side of rib 26 are a first bearing 34 and a second bearing 36. The bearings can be conventional roller bearings or other suitable bearings, as desired. A bottom ratchet plate 38 is also provided for the knee joint. Bottom ratchet plate 38 is depicted in greater detail in FIGS. 3A and 3B. Bottom ratchet plate 38 includes a planar bottom surface 40, as illustrated in FIG. 3B, and a top face 42 having a plurality of radially extending spaced teeth 44 protruding therefrom. As is evident from FIG. 3A, sixty such teeth 44 are preferably located on the top face 42 with each tooth being spaced from the adjacent teeth by slots, although any suitable number of teeth can be utilized. Preferably, the teeth 44 are cut in a saw tooth pattern radially at a 30 degree is slope. A set of eight spaced slots 46 are cut into the bottom ratchet plate 38. The slots extend radially outwardly from a central opening 48 of the plate 38 as is evident from FIG. 3A.

The joint of FIGS. 1A and 1B is further provided with a top ratchet plate 50, which is shown in more detail in FIGS. 4A and 4B. Top ratchet plate 50 is preferably constructed of a magnetically soft material, for example a low hysteresis, solenoid quality magnetic stainless steel. Bottom plate 38 may be constructed of similar material. With reference now to FIG. 4B, top ratchet plate 50 includes a top face 52 (FIG. 4B) and a bottom face 54. A plurality of spaced teeth 56 are cut into the bottom face 54. Preferably sixty such teeth are provided. As with the bottom plate 38, the teeth 56 in the top plate are cut in a saw tooth pattern radially at a 30 degree slope such that a tip of each tooth is separated from a tip of each adjacent tooth by 6 degrees. Teeth 56 of top ratchet plate 50 are meant to be and should be of suitable design and number to engage and mesh with teeth 44 of bottom ratchet plate 38 when the two ratchet plates are brought into contact with each other. Also provided on top ratchet plate 50 is a slot 58 which circumscribes the teeth 56. A plurality of spaced apertures 60' extend through top ratchet plate 50. These apertures are positioned radially outwardly of slot 58. As is evident from FIGS. 1B and 10, suitable fasteners 60 can extend into the top ratchet plate apertures.

With reference now to FIGS. 1A, 1B and 10, a shaft 62 is also provided. As shown in FIGS. 5A and 5B shaft 62 includes a stem portion 64 and an enlarged top end 66 having a set of spaced apertures 68 extending therethrough. Note that in FIGS. 5A and 5B, the diameter of flange 66 is illustrated smaller than the diameter illustrated in the other figures. A bottom end of the stem portion 64 is provided with a centrally located aperture 70. Each of these apertures accommodates suitable fasteners 60 and 61. Referring to FIGS. 1A and 1B, also provided is an inner retaining ring 72. As detailed in FIG. 6, inner retaining ring 72 has a central aperture 72' for accommodating stem portion 64 and includes a set of apertures 74 extending therein. Each of apertures 74 is also meant to accommodate a suitable fastener 60. A retaining cap 76 is also provided. As shown in FIGS. 7 and 7A, retaining cap 76 has a centrally extending aperture 78 for accommodating a suitable fastener 61. Fasteners 60 and 61 can be threaded fasteners or any other suitable type of fastener, for example.

Figure 8:
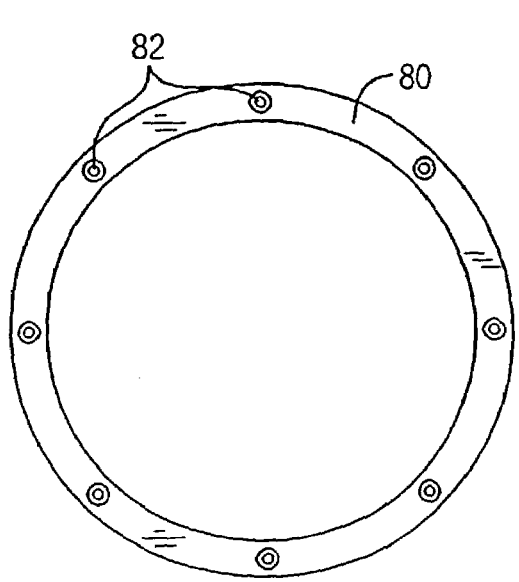
FIG. 8 is a top plan view of an outer retaining ring of the joint of FIG. 1A.
Figure 9:
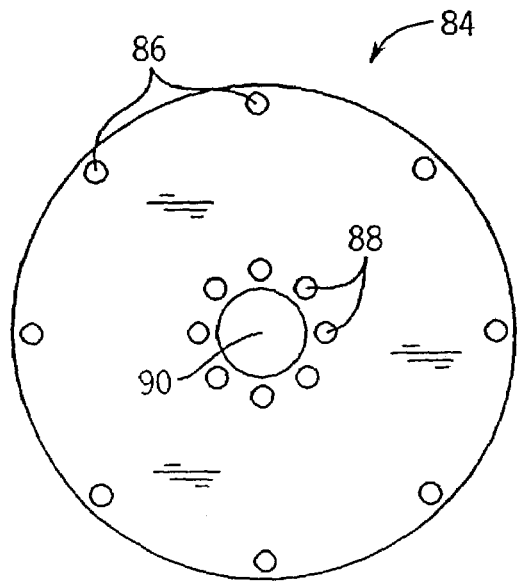
FIG. 9 is a top plan view of a spring washer of the joint of FIG. 1A.

Joint 10 is also provided with an outer retaining ring 80. As shown in FIG. 8 a set of apertures 82 extend through retaining ring 80 to accommodate suitable fasteners 60. As shown in FIGS. 1A, 1B, 9 and 10, a spring washer 84 is further provided. Spring washer 84 is preferably comprised of a plurality of very thin pieces of metal which, when assembled, is very compliant in an axial direction while maintaining a high rigidity in torsion. For example, spring washer 84 may consist of approximately 60 pieces of 0.001 inch thick stainless steel disks. The axial compliance allows the spring washer to be deflected at relatively low electromagnetic forces allowing the upper ratchet plate to mesh with the lower ratchet plate. Spring washer 84, further depicted in FIG. 9, has a set of outer apertures 86 for accommodating a suitable first set of fasteners 60 and a set of inner apertures 88 similarly for accommodating a suitable second set of fasteners 60. Spring washer 84 also has a central opening 90 to accommodate stem portion 64 of shaft 62.

Spring washer 84 is very compliant in the axial direction, permitting deflection of upper ratchet plate 50 even with relatively low electromagnetic attraction forces, typically deflecting about $\frac{1}{16}^{th}$ of an inch in an axial direction with an electromagnetic force of several pounds. Thus, the significant axial deflection that is obtained with low electromagnetic forces permits operation of joint 10 at low power consumption levels which is important for battery-operated use. Spring washer 84, however, is strong and stiff in torsion, providing the necessary reaction torque to support the moments required in an orthotic application. Any suitable washer that performs the function of spring washer 84 can be utilized in accordance with the invention.

As is evident from FIGS. 1A, 1B and 10, shaft 62 is located in central opening 28 of toroidally shaped housing 12. Retaining cap 76 is fastened to shaft 62 by fastener 61. In this way, two bearings 34 and 36 can be secured in place in central opening 28 of housing 12. Bottom ratchet plate 38 is seated on inner wall 14 of housing 12. To this end, several spaced slots 46 in bottom ratchet plate 38 accommodate several spaced teeth 22 in housing 12. More particularly, eight slots 46 and eight teeth 22 are provided in housing 12. It is apparent that no keying is necessary since bottom ratchet plate 38 can be rotated in relation to the housing to any desired extent so long as the slots 46 are aligned with teeth 22.

Top ratchet plate 50 is positioned above bottom ratchet plate 38. In the condition illustrated in FIG. 1A, top ratchet plate 50 is spaced from bottom ratchet plate 38. This allows a movement of joint 10 in either rotational direction (flexion or extension). In the position illustrated in FIG. 1B, the teeth of top ratchet plate 50 engage the teeth of bottom ratchet plate 38 to prevent any further rotation of the joint. Preferably, the two ratchet plates are spaced from each other as indicated when in the unactuated state as shown in FIG. 1A.

With reference again to FIG. 1A, spring washer 84 is fastened to flange 66 of shaft 62 via inner retaining ring 72.

Spring washer 84 is also fastened to top ratchet plate 50 and outer retaining ring 80 by fasteners 60. In this way, top ratchet plate 50 is normally spring-biased away from bottom ratchet plate 38. However, top ratchet plate 50 is pulled into contact with bottom ratchet plate 38 when electromagnetic current is flowing through electromagnetic coil 30.

Figure 11:
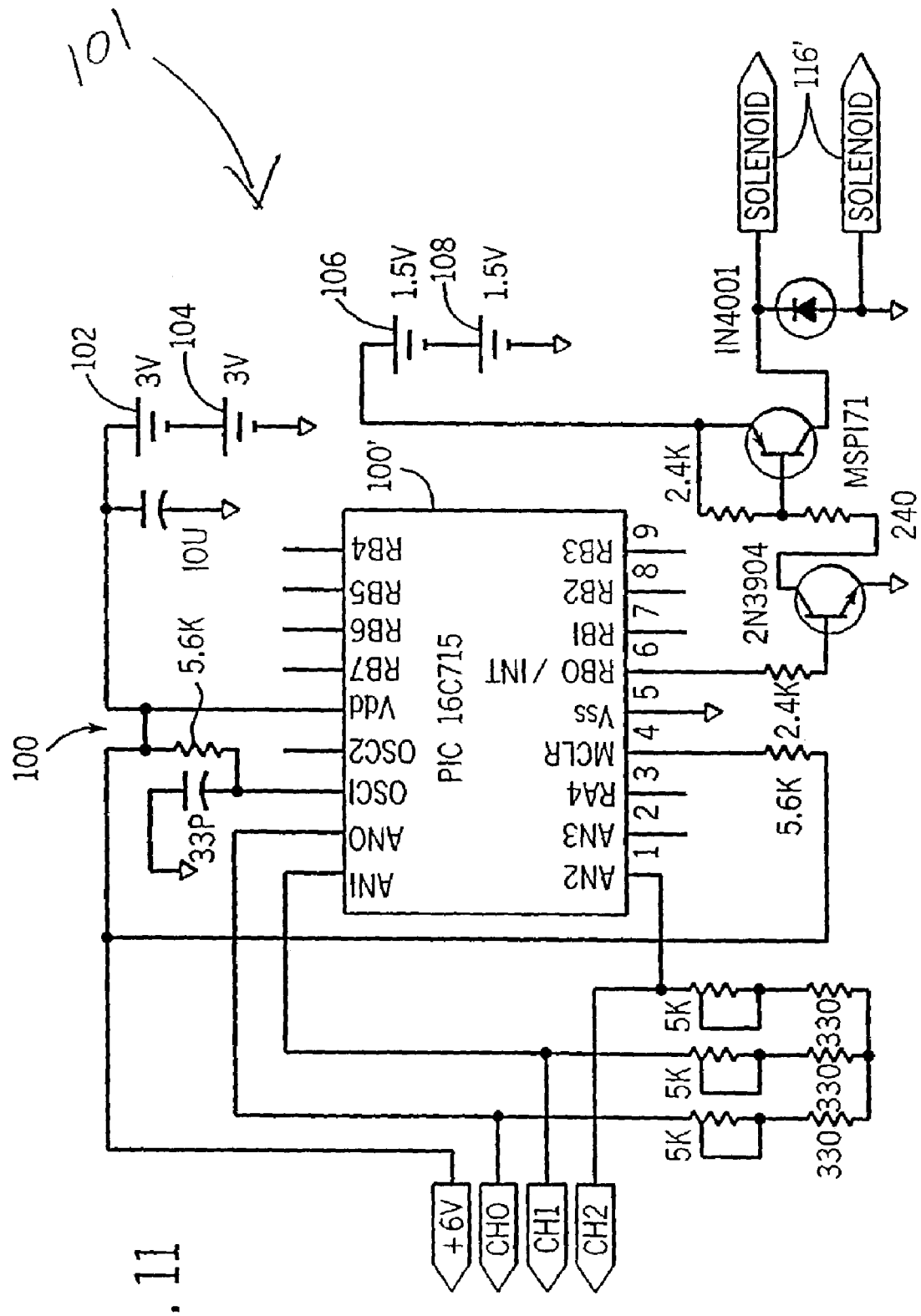
FIG. 11 is a circuit diagram of a circuit which is employed with the knee joint of FIG. 1A and the force or pressure sensor of FIG. 12.

With reference now to FIG. 11, a controller 101 which includes an integrated circuit 100', which can be a Microchip Model No. PIC16C715, is employed to control the operation of joint 10. The integrated circuit is preferably powered by a pair of 3 volt batteries 102 and 104. Electromagnetic coil 30 is preferably powered by a pair of 1.5 volt batteries 106 and 108.

With reference now to FIG. 12, an insole pressure or foot force sensor 110 is also used in connection with the joint 10. More particularly, a set of output lines 112 lead from a set of sensors 114 in the insole to circuit 100. Batteries 102 and 104 provide a reference signal for the sensors. A pair of output lines 116' from circuit 100 extend to the electromagnetic coil 30. The pair of 1.5 volt batteries 106 and 108, which are of relatively higher power than the power of the 3 volt batteries, are meant to power the electromagnetic coil.

Insole pressure sensor 110 is preferably provided with five sensors which detect pressure by a voltage drop across very thin resistors, for example the foot force sensor provided by Cleveland Medical Devices, Inc. It should be apparent to one skilled in the art that more or less sensors may be used. The insole is slipped inside a patients shoe. The signal from the insole is translated through wires 112 to circuit 100. Integrated circuit 100' also contains a programmable microprocessor. Any suitable microprocessor can be utilized. The processor determines a threshold level and sends a signal to the joint 10 attached to a knee joint as depicted in FIG. 13. However, the joint need not be limited to a knee joint, but may also be an ankle, wrist or elbow joint. Any suitable pressure or force sensor can be used in accordance with the invention.

With the orthosis of the present invention, when a person puts his foot on the floor, the sensors 114 in insole sensor 110 sense a pressure and can trigger the joint 10 to lock by energizing electromagnetic coil 30 thereby bringing the top ratchet plate 50 down into contact with bottom ratchet plate 38 engaging respective teeth 56 and 44. Preferably, this action prevents any further rotation of the joint in one rotational direction, however, this may lock the joint entirely from rotating. More particularly, top ratchet plate 50 and shaft 62 cannot rotate via bearings 34 and 36 in relation to bottom ratchet plate 38 and housing 12 toward a bent knee position. Preferably, when the teeth of the upper and lower ratchet plates are engaged, the joint allows incremental slip (ratcheting) in a joint extension. However, when no more pressure is sensed by sensors 114 of the insole sensor 110, controller 101 will unlock the knee joint by ceasing the flow of electric current in the electromagnetic coil.

Once this occurs, spring washer 84 will pull top ratchet plate 50 out of engagement with bottom ratchet plate 38. This will allow a rotation of the knee joint in both directions. In particular, top ratchet plate 50 and shaft 62 are again capable of rotating in relation to bottom ratchet plate 38 and housing 12. Thus, the joint is unlocked when pressure of the patient's foot is no longer exerted on the insole sensor 110. This invention will allow a user who is currently wearing stiff legged knee/ankle/foot orthoses to walk with a more normal gait. In addition, it will make sitting and standing safer and easier for any user currently forced to manually unlock their knee joint.

When a threshold level is reached, a magnetic field is generated by electromagnetic coil 30 to pull top ratchet plate 50 into engagement with bottom ratchet plate 38, no longer allowing the two ratchet plates to rotate freely in relation to each other. This locks the knee joint and prevents it from bending into flexion. However, the joint will still allow extension. As an example, if the patient is attempting to stand and gets stuck halfway up, the joint will block flexion and prevent the patient's knee from buckling. But, it will still ratchet into extension and allow the patient to continue moving vertically. Thus, a very important advantage of the present invention is the provision of a knee joint in which flexion is prevented when the top ratchet plate 50 meshes with bottom ratchet plate 38 but extension is still allowed. This is accomplished due to the orientation of the meshing teeth 44 and 56 of the bottom and top ratchet plates 38 and 50 respectively.

As a second example, a user, when he takes a step, will have the insole read the floor contact and lock the knee for the user. The knee remains locked through the step and then unlocks when the user initiates swing through, i.e. takes the pressure off the first leg and puts the pressure on the second leg. The knee joint will then lock again at the next initial floor contact.

Sensors 114 could be wired in series or in parallel for the signal which is sent through wires 112 to controller 101. Preferably, the output of all of sensors 114 is summed together. If a set point is reached, electromagnetic coil 30 is triggered and the knee joint is locked. However, the logic of the chip on the integrated circuit could be programmed to differentiate between, e.g. a heel strike and a toe strike of the foot plate. The logic of the circuit may also provide that given patterns of pressure, for example placing pressure on only inner or outer pressure sensors, detected by the sensors could disengage the teeth in the joint permitting an individual to sit.

Joint 10 according to the present invention can be attached to any conventional knee/ankle/foot/elbow/wrist orthosis or any knee brace as long as the brace is fabricated to the joint size specification. A person skilled in the art should realize that the orthotic joint of the present invention supports passive locking arrangements wherein the joint is locked until the coil is magnetized which unlocks the joint as opposed to the active locking embodiment of the joint as described above.

FIGS. 14 and 15 illustrate an alternate embodiment of an electronically controlled orthotic joint according to the present invention. This embodiment as shown in FIGS. 14 and 15 provides an electromagnetic coil 118 located within a housing 120. Actuating portion 122 is provided as well as opposing teeth inserts 124 and 126. Engagement of the teeth inserts 124 and 126 is actuated by energizing coil 118. The coil is energized under control of a microprocessor (not shown) as in the above embodiment. Energizing the coil produces an axial force on actuating portion 122 which forces teeth insert 124 into engagement with teeth insert 126. In this embodiment, a passive spring (not shown) causes the teeth of teeth inserts 124 and 126 to disengage upon interruption of current through coil 118. This embodiment can also provide for incremental slip in a single rotational direction as desired. Further, teeth inserts 124 and 126 are constructed of non-magnetic material so that they may be made of a more durable material, for example tool steel. This embodiment also provides a spline interface (not shown) between outer support ring 130 and actuating element 122. This spline interface is on the internal surface of outer support ring 130 and the external surface of actuating element 122. This spline interface permits axial translation of actuating element 122 while enabling large torques to be transmitted from outer support ring 130 to actuating element 122. This arrangement permits application of large torques from outer support ring 130 to the opposite outer support ring 128 as follows. Torques are transmitted from element 130 to element 122 via the spline interface. Torques are thus transmitted from actuator element 122 to teeth insert 124, which is fastened rigidly to element 122. When engaged due to actuation (axial translation of element 122), teeth insert 124 meshes with teeth insert 126 enabling transmission of torques that oppose knee flexion. Teeth insert 126, rigidly fastened to housing 120, transmits torques to housing 120 via its fasteners. Finally, housing 120, which is rigidly fastened to outer support ring 128, transmits torque to outer support ring 128 via fasteners (not shown). In this manner, torques can be transmitted from support arm 132 of outer support ring 130 to support arm 134 of the opposite outer support ring 128. Support arms 132 and 134 provide a convenient structure to mechanically interface the locking mechanism to orthotic bracing. One skilled in the art should recognize that an equal and opposite torque is transmitted to outer support ring 128 and support arm 134 in a similar manner.

Referring to FIG. 14, a stop 136, which can be integral to outer support arm 132, and a complementary stop (not shown), approximately 180° away from stop 136, acts to interface with arm 134 to mechanically limit the range of relative rotation between outer rings 128 and 130. This feature can be used to prevent hyperextension.

FIG. 14 depicts how joint 117 is integrated into an orthotic device. Outer support rings 128 and 130 house joint 117. As shown in FIG. 14, joint 117 is comprised of an electromagnetic coil 118, housing 120, actuating portion 122, and teeth inserts 124 and 126. The outer support rings are constructed of non-magnetic metallic material. Outer support ring 130 has an attached support arm 132 which attaches to a limb portion of a patient. Similarly, outer support ring 128 has a support arm 134 that attaches to the same limb portion of a patient as support arm 132, but joint 117 is aligned with the patient's joint which is to be supported.

Figure 16:
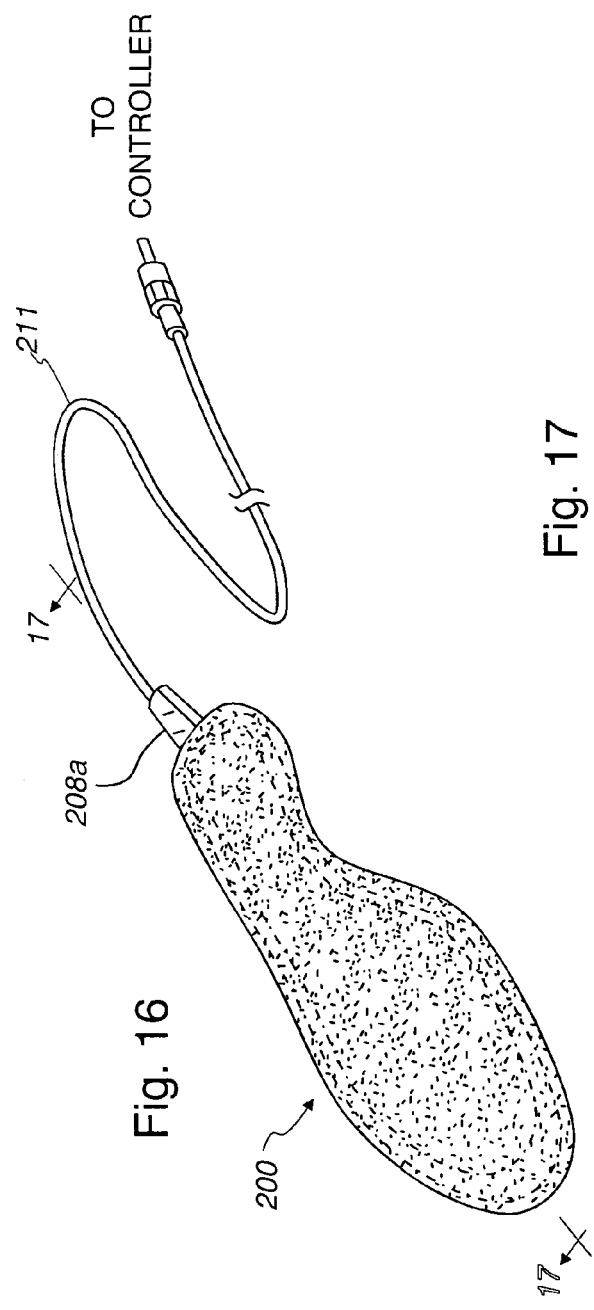
FIG. 16 illustrates a perspective view of an alternate embodiment of a foot sensor in accordance with the invention.
Figure 17:
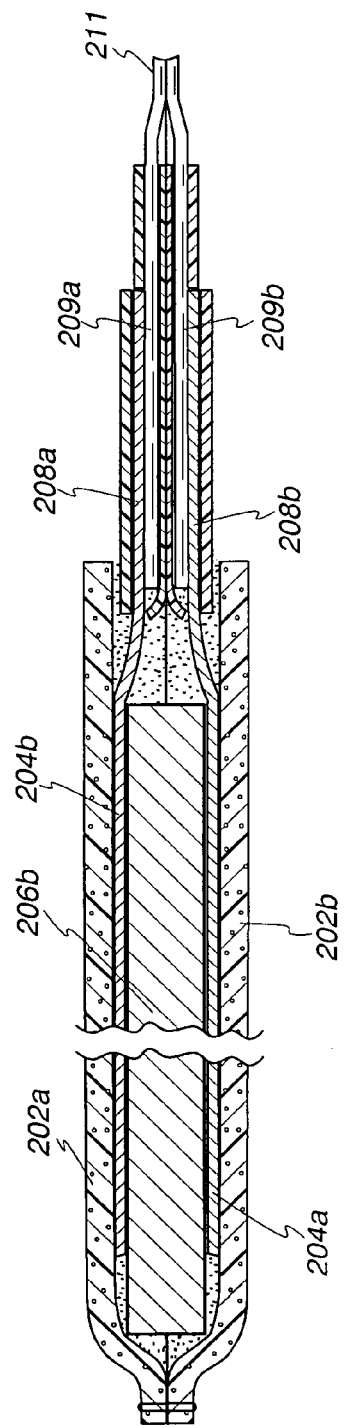
FIG. 17 is a sectional view of the foot sensor taken along line 17-17 of FIG. 16.

FIGS. 16-20 show alternate embodiments of foot sensors in accordance with the present invention. These foot sensors can be utilized in orthosis 10' in place of foot force sensor 110 together with any desired or needed changes to or replacements for controller 101 or circuit 100, or to joints 10 or 117, as will be evident to those skilled in the art. In FIGS. 16-18, a foot sensor 200 is provided and may be configured in the general shape of a shoe insole suitable to fit into the shoe of a person wearing orthosis 10'. Foot sensor 200 preferably includes moisture barrier 202a and 202b, conductive layers or plates 204a and 204b, and a layer 206 of variably resistive material as best seen in FIG. 18. Layer 206 is typically elongated and relatively thin. Layer 206 of variably resistive material includes a plurality of small conductive particles dispersed or suspended as normally discontinuous phase within a resilient compressive material such as rubber. The conductive particles may be any suitable conductive material as is commonly known in the art. Examples include, but are not limited to, conductive metal, carbon or graphite. The material of layer 206 displays high resistance or is otherwise insulative when in an uncompressed state. When a compressive force or pressure above a threshold force is applied normal to an area of layer 206, the conductive particles contact each other, lowering the resistive state in that area, making the variably resistive material of layer 206 conductive in that area. Within design limits or variations for the material, a force or pressure equal to or below the threshold force in that area may compress layer 206 to some extent. It is understood, however, again within design limits or variations for the material, that a force equal to or below the threshold force will not adequately lower the resistance of layer 206 to make layer 206 conductive. Layer 206 can be continuous or discontinuous and its presence in a particular area of foot sensor 200 provides an area that will sense pressure.

Conductive layers or plates 204a and 204b sandwich the layer 206 of variably resistive material so as to be in operative communication with layer 206 as shown in FIGS. 17 and 18. Plates 204a and 204b are preferably thin, malleable sheets of metal foil with resilience to withstand compressive forces from the foot of a person during activities such as standing, walking, climbing stairs and moving from a sitting to a standing position or vice versa. It is understood that any type of metal or conductive material may be used for conductive plates 204a and 204b with brass, copper, aluminum, steel or stainless steel preferred. Most preferred are 0.002 inch brass plates 204a and 204b. Each conductive plate 204a and 204b may take other forms including, but not limited to, a mesh, a screen, a wire, a plurality of wires or any combination of the same.

Electrodes 208a and 208b (FIG. 17), which may be integral to conductive plates 204a and 204b respectively, extend from plates 204a and 204b respectively to provide a surface upon which wires 209a and 209b may be attached. Wires 209a and 209b extend to controller 101 as cord 211. Contact between electrodes 208a and 208b and wires 209a and 209b may be established by any suitable means as commonly known in the art, including but not limited to, soldering or securing in place with insulative tape. Electrodes may be protected by means commonly known in the art such as with insulative tape or a plastic sleeve, for example. FIG. 16 shows electrodes 208a and 208b extending from the heel portion of sensor 200 although it is understood that electrodes 208a and 208b can extend from any area of sensor 200.

Moisture barriers 202a and 202b encase the layer 206 of variably resistive material and conductive plates 204a and 204b. Moisture barriers 202a and 202b are made from a water-resistant or water repellent material such as, but not limited to, rubber or flexible plastic. This protects plates 204a, 204b and layer 206 from foot moisture, or external types of wetness typically encountered when wearing shoes outdoors such as water seepage from rain or puddles, for example. Moisture barrier 202a is attached to moisture barrier 202b by any suitable means as is commonly known in the art such as adhesively bound, stitched or a combination thereof. Alternatively, moisture barriers 202a and 202b may be integral to each other. In any event, moisture barriers 202a and 202b are made of an insulative, non-conductive material. One suitable moisture barrier is marketed under the name DYCEM® by Dycem USA of Rhode Island.

Provision of a force above the threshold force by the foot of a person onto sensor 200 (i.e., normal to the surface of sensor 200) brings the conductive particles of layer 206 into contact yielding a conductive path or a plurality of conductive paths through layer 206. This establishes a closed circuit between conductive plates 204a and 204b and controller 101. Controller 101 then generates and sends a control signal to orthotic joint 10 as long as a compressive force greater than the threshold force, i.e., an actuation force, is maintained on sensor 200. A compressive force less than or equal to the threshold force fails to adequately reduce the resistance of layer 206 thereby opening the circuit between conductive plates 204a and 204b. This terminates generation of the control signal by controller 101. It is understood that plates 204a and 204b may be considered one component which closes the circuit when an actuation force is applied upon sensor 200.

FIGS. 17 and 18 show one embodiment of sensor 200 wherein plates 204a, 204b are substantially coextensive with the layer 206 of variably resistive material. An actuation force anywhere on the surface of plate 204a coextensive with plate 204b and layer 206 will close the circuit between plate 204a, layer 206 and plate 204b and thereby generate a control signal. In like manner, a plurality of actuation forces anywhere upon the surfaces of plates 204a and 204b will close the circuit between plates 204a and 204b. The skilled artisan will recognize that layer 206 may incorporate any number of resilient compressive materials thereby providing a wide range of possible resistances and concomitant actuation forces as desired.

In an alternate embodiment, a sensor 210 comprises a conductive plate or layer 212 in communication with layer 206 of variably resistive material as shown in FIG. 19. Conductive plate 212 is shaped to communicate with layer 206 at discrete zones or contact points. Conductive layer 212 comprises a heel zone 214, a front zone 216 and a connecting portion 218 connecting the two zones. It is understood that the conductive plate on the underside of sensor 210 may be the same shape as conductive plate 212 or may be substantially coextensive with layer 206 or to the entire overall extent of sensor 210. Similarly, layer 206 may be modified to conform to the shape of conductive plate 212 or to only portions thereof (not shown), for example, such as to only a portion of heel zone 214 and front zone 216. An actuation force or a plurality of actuation forces occurring anywhere along the surfaces of zones 214 and 216 or connecting portion 218 where layer 206 is present will produce a closed circuit with layer 206 and the underside conductive plate thereby generating a control signal. Sensor 210 may be enclosed in a water-resistant material as previously described.

FIG. 20 depicts an alternate embodiment of a sensor 220 in accordance with the invention. A conductive plate 222 communicates with layer 206 of variably resistive material at a plurality of toe zones 224a-c, a heel zone 226 and a connecting portion 228. The conductive plate (not shown) on the underside of layer 206 may be the same shape as conductive plate or layer 222 or may be substantially coextensive with material 206. Alternatively, layer 206 may be modified to replicate the shape of conductive plate 222 or desired portions thereof, such as toe zones 224a-c and heel zone 226. Thus, layer 206 may be discontinuous. An actuation pressure or a plurality of actuation pressures anywhere along the surfaces of toe zones 224a-c, heel zone 226 or connection portion 228 (if layer 206 is present thereunder) will produce a closed circuit through at least a portion of layer 206 and the underside conductive plate is thereby producing a control signal. Sensor 220 may be encased with a water-resistant material as previously described.

A suitable material for layer 206 is sold under the name ZOFLEX by Xilor, Inc. of Knoxville, Tennessee. ZOFLEX is a pressure sensitive conductive rubber having high resistance when an applied force or pressure is below the actuation pressure. Typical thickness for such material is in the range of about 0.02 to 0.06 inches.

The control signal generated when an actuation force is placed upon the sensor may be uniform or variable. A uniform control signal is generated when the pressure sensitive conductive component has uniform resistance. In this arrangement, layer 206 acts as an on/off switch and remains in a non-conductive state until a compressive force greater than the threshold force is applied to the sensor. When an actuation force is applied to the sensor, the circuit is closed between the conductive layers or plates and controller 101. Consequently, controller 101 generates a constant control signal uniform in signal strength. Hence, regardless of the sensor area exposed to the actuation force or the magnitude of the actuation force in excess of the threshold force, the signal produced by controller 101 remains constant. In this arrangement, the control signal pulls the top ratchet plate 50 into contact with bottom ratchet plate 38 thereby locking joint 10 in at least one rotational direction. Orthotic joint 10 may be configured to allow extension but prevent flexion or prevent extension and allow flexion or prevent both extension and flexion as desired. A force less than or equal to the threshold force terminates generation of the control signal thereby unlocking joint 10.

In an alternate embodiment, the control signal may be variable in strength. This occurs when the layer of variable resistant material has a variable resistance as a function of a pressure or force applied thereto in a direction normal to the surface of the layer. In other words, the conductivity of layer 206 is proportional to the compressive force applied to the sensor. Once the threshold force is exceeded, additional compressive force applied to the sensor or an increase in the area of the sensor exposed to an actuation force increases the conductivity of layer 206. In this embodiment, controller 101 produces a low strength control signal when a force just above the threshold force is applied. The control signal gains in strength as the compression force upon the sensor increases. The greater the compression of layer 206, the greater the control signal strength and vice versa. The size of the sensor area exposed to the actuation force may also be used to determine the control signal strength in like manner. In any case, an orthotic joint may be configured and used to receive the variable control signal. An orthotic joint may be configured in a manner known in the art to produce incremental or gradual resistance to motion proportional to the strength of the control signal. For example, top plate 50 and bottom plate 38 may have rounded or smooth teeth or no teeth at all. As the magnitude of the actuation force increases, top plate 50 and bottom plate 38 contact each other to provide resistance to motion in at least one rotational direction. This resistance to motion increases as the actuation force increases and decreases as the actuation force decreases. Joint 10 may be configured to fully lock upon reception of a defined control signal strength or maximum signal strength. Alternatively, a frictional resistance type joint may be used where the amount of frictional resistance is proportional to the strength or weakness of the control signal as desired.

One of ordinary skill in the art will realize that many factors may influence the threshold force of the sensor. For example, it is desirable to adjust the threshold force of the sensor to accommodate the size and/or weight of the person using or wearing orthotic device 10'. The threshold force may be adjusted by selecting materials having differing resistances for the variably resistive material component or by programming controller 101. Correspondingly, the sensor threshold force may be lower for a child or an elderly person than for an adult male, for example. The anticipated activity of the wearer may also be taken into account and the device adjusted accordingly.

In addition, the sensor may be adapted to accommodate the degree of ambulation and/or gait of the orthotic wearer. The pressure points upon the foot sensor may vary dramatically between wearers. For example, a person having a foot or a foot/leg prosthesis may have a different foot pressure profile than a person having a natural foot. In an alternate embodiment, the sensor comprises a layer of variably resistive material divided into a plurality of discrete regions. The regions may be directly adjacent to each other. Alternatively, any space between the discrete regions of variably resistive material may be filled by a non-conductive substrate shaped to conform to the insole of a shoe. Each region may correspond to foot pressure points adaptable to the specific needs of the user. The regions may include, but are not limited to, a toe region, a metatarsal region, and a heel region, for example. Each region may be further divided into sub-regions—i.e., a region for each toe or front and rear heel sub-regions, for example. Each region or sub-region may comprise variably resistive material having differing threshold forces as dictated by the needs of the orthotic device wearer. In addition, the sensor may include regions composed of variably resistive material having either uniform or variable resistance. Thus, the combinations between types of variably resistive material, the number and size of regions, and the threshold force for each region is virtually unlimited. For example, variably resistive material having uniform resistance may be used at strong pressure point regions, such as the heel region or the metatarsal region. This arrangement is useful so that ordinary leg and foot movement that occurs during sitting will not yield an actuation force and subsequent generation of a control signal. As the wearer begins to stand, the shift in weight to the foot sensor produces an actuation force and a concomitant uniform control signal. Device 10' is preferably configured to prevent flexion but allow extension movement upon receipt of this control signal.

During walking, an actuation force anywhere along the sensor may generate a uniform control signal. It is understood that different regions of the sensor may comprise variably resistive material requiring differing actuation forces. For example, the heel region may require a greater actuation force than the toe region.

Alternatively, variably resistive material with variable resistance may also be used on the heel region, the metatarsal region and the toe region. Each region may be configured to require a different actuation force as desired. During the walking cycle, for example, an actuation force on the heel region may occur as the heel first contacts the walking surface. This initial force may generate a variable control signal limiting, but not preventing, flexion movement of the lower leg with the signal gaining in strength as the heel region receives greater force. As the walker's weight transfers to the metatarsal region of the foot, an actuation force may generate a variable signal which combines with the signal from the heel region to completely lock joint 10. As weight transfers off of the heel region to the metatarsal region and toe regions, the reduction in force on the heel region may reduce the signal strength of the control signal thereby allowing flexion movement. Continuing through the walking cycle, a reduction in force on the metatarsal region may further reduce the signal strength allowing more flexion movement. As pressure is relieved from the toe region, the control signal may terminate allowing unrestricted movement of the lower leg. As a safety feature, the orthotic device may be equipped with an override switch that either locks or unlocks the knee joint regardless of whether a control signal is present.

The sensor may be readily applied to other orthotic devices. For example, the foot sensor may be connected to an ankle orthosis having a selectively lockable ankle joint. A control signal may be generated to lock or otherwise restrict movement in the ankle joint upon the occurrence of an actuating pressure on the foot sensor. Similarly, the sensor may also be adapted to an elbow orthotic device. An actuating pressure on variably resistive sensors located on the palm and/or fingers of a hand or hand prosthesis may send a control signal to a selectively lockable elbow joint restricting or preventing movement of the elbow. The hand sensors may also send a control signal to a selectively lockable wrist joint in a similar manner. In like manner, a back brace may be configured with a sensor wherein the threshold pressure is exceeded restricting movement when the back brace wearer is in the sitting or prone position.

While the invention has been described with respect to certain preferred embodiments, as will be appreciated by those skilled in the art, it is to be understood that the invention is capable of numerous changes, modifications and alterations that are within the scope of the appended claims.

What is claimed is:

1. A selectively operable orthotic device comprising:
   (a) a thin elongated layer of variably electrically resistive material having two sides, said variably electrically resistive material capable of exhibiting changed electrical resistance through an area of the thin layer to which a compressive force normal to the thin elongated layer and above a threshold level is applied;
   (b) a first conductive element in electrical contact with a first side of an area of said thin layer of variably electrically resistive material that is to be sensed;
   (c) a second conductive element in electrical contact with a second side, opposite the first side of the area of said thin layer of variably electrically resistive material that is to be sensed;
   (d) an electronic circuit operatively connected to said conductive elements, said circuit generating a control signal when more than the threshold compressive force is applied to at least part of the area of said variably electrically resistive material that is to be sensed; and
   (e) an orthotic device operatively connected to said electronic circuit, said device having a mechanism selectively switchable from one state to another state in response to said signal.

2. The device of claim 1 wherein each conductive element comprises an element selected from the group consisting of a thin continuous layer of conductive material, a thin discontinuous layer of conductive material, a wire and a network of wires.

3. The device of claim 2 wherein each conductive element is coextensive with said variably electrically resistive material and said first and second conductive elements form an electrical conductive pathway through at least a portion of the area with the layer of variably electrically resistive material.

4. The device of claim 1 wherein said variably electrically resistive material is responsive to the force from a person's foot or foot prosthesis and said mechanism is a selectively lockable knee joint.

5. The device of claim 4 wherein the variably electrically resistive material has uniform conduction above the threshold compressive force and said circuit generates an associated uniform control signal.

6. The device of claim 5 wherein the mechanism locks the knee joint in the presence of the control signal and unlocks the knee joint in the absence of the control signal.

7. The device of claim 6 wherein the layer of variably electrically resistive material exhibits a decrease in resistance upon application of a sufficient force.

8. The device of claim 7 wherein the sufficient force is a force above a threshold level.

9. The device of claim 7 wherein said layer of variably electrically resistive material further comprises at least one discrete area selected from the group consisting of a toe area, a sub-toe area, metatarsal area, a sub-metatarsal area, a heel area, a sub-heel area and combinations thereof.

10. The device of claim 9 further comprising a non-conductive substrate substantially coextensive with the foot or foot prosthesis of a person for maintaining said at least one discrete area of said layer of variably electrically resistive material in electrical contact with said conductive elements.

11. The device of claim 9 wherein the threshold force is different for at least two discrete areas.

12. The device of claim 7 wherein at least one conductive element further comprises at least one discrete zone selected from the group consisting of a toe zone, a sub-toe zone, a metatarsal zone, a sub-metatarsal zone, a heel zone, a sub-heel zone and combinations thereof.

13. The device of claim 12 wherein each said at least one discrete zone of the conductive element contacts a corresponding discrete area of said layer of variably electrically resistive material.

14. The device of claim 6 wherein said mechanism further comprises two opposing plates with intermeshing teeth, said teeth rigidly locking to prevent flexion but allowing extension in response to the control signal, said teeth disengaging allowing flexion and extension in the absence of the control signal.

15. The device of claim 4 wherein the variably electrically resistive material has variable conduction and said circuit generates a variable control signal which increases and decreases in strength corresponding to increases and decreases in force applied to the variably electrically resistive material.

16. The device of claim 15 wherein said mechanism increases and decreases resistance to motion in the knee joint responsive to corresponding increases and decreases in the control signal strength.

17. The device of claim 16 wherein said mechanism locks the knee joint responsive to a maximum control signal strength.

18. The device of claim 17 wherein the layer of variably electrically resistive material is substantially coextensive with the foot of a person.

19. The device of claim 18 wherein at least one conductive element is substantially coextensive with the layer of variably electrically resistive material.

20. The device of claim 19 wherein said layer of variably electrically resistive material further comprises at least one discrete region selected from the group consisting of a toe region, a sub-toe region, a metatarsal region, a sub-metatarsal region, a heel region, a sub-heel region and combinations thereof.

21. The device of claim 20 further comprising a non-conductive substrate substantially coextensive with the foot or foot prosthesis of a person for maintaining at least one discrete region of said layer of variably electrically resistive material in electrical contact with said conductive elements.

22. The device of claim 20 wherein the threshold force is different for at least two regions.

23. The device of claim 19 wherein at least one conductive element further comprises a plurality of discrete zones selected from the group consisting of a toe zone, a sub-toe zone, a metatarsal zone, a sub-metatarsal zone, a heel zone, a sub-heel zone and combinations thereof.

24. The device of claim 23 wherein each said at least one discrete zone of the conductive element contacts a corresponding discrete region of said layer of variably electrically resistive material.

25. The device of claim 16 wherein said mechanism further comprises two opposing plates, said plates frictionally engaging and variably resisting flexion but permitting extension responsive to the variable control signal strength and permitting flexion and extension movement in the absence of the control signal.

26. The device of claim 1 further comprising a moisture barrier encapsulating the layer of variably electrically resistive material and the conductive elements.

27. The device of claim 26 wherein the moisture barrier is essentially water-resistant.

28. The device of claim 1 wherein said variably electrically resistive material comprises conductive particles suspended in a resilient material.

29. A method for selectively operating an orthotic device associated with the joint of a person comprising:
(a) providing a thin elongated layer of variably electrically resistive material capable of changing electrical resistance responsive to a change in the application of a force above a threshold force to at least a portion of said layer, said layer having opposing upper and lower surfaces;
(b) electrically contacting a conductive element with said surfaces;
(c) generating a control signal with an electronic circuit operatively connected to the conductive element when a threshold force is applied to the variably electrically resistive material; and
(d) selectively switching the mechanism of an orthotic device from one state to another state in response to the control signal.

30. The method of claim 29 wherein said providing comprises providing variably electrically resistive material that exhibits decreased electrical resistance through an area of the thin layer to which a compressive force normal to the thin layer and above a threshold level is applied.

31. A selectively operable orthotic device comprising:
(a) a thin elongated layer of variably electrically resistive material capable of decreasing electrical resistance responsive to the application of a force above a threshold force to at least a portion of said layer, said layer having opposing upper and lower surfaces;
(b) a conductive element in electrical contact with said surfaces;
(c) an electronic circuit operatively connected to said conductive element, said circuit generating a control signal when an actuating force is applied to said variably electrically resistive material; and
(d) an orthotic device operatively connected to said electronic circuit, said device having a mechanism selectively switchable from one state to another state in response to said signal.

* * * * *